United States Patent
Hyde et al.

(10) Patent No.: US 7,595,150 B2
(45) Date of Patent: Sep. 29, 2009

(54) METHOD OF APPLYING AN ELONGATED MOLECULE TO A SURFACE

(75) Inventors: Roderick A. Hyde, Livermore, CA (US); Lowell L. Wood, Jr., Livermore, CA (US)

(73) Assignee: Searete LLC, Bellevue, WA (US)

( * ) Notice: Subject to any disclaimer, the term of this patent is extended or adjusted under 35 U.S.C. 154(b) by 0 days.

(21) Appl. No.: 11/480,779

(22) Filed: Jun. 30, 2006

(65) Prior Publication Data

US 2008/0003613 A1 Jan. 3, 2008

Related U.S. Application Data

(63) Continuation-in-part of application No. 11/480,820, filed on Jun. 30, 2006, and a continuation-in-part of application No. 11/480,763, filed on Jun. 30, 2006.

(51) Int. Cl.
*C12Q 1/00* (2006.01)
(52) U.S. Cl. .......................................... 435/4
(58) Field of Classification Search ............ 435/4, 435/7.1, 7.92; 436/514, 518
See application file for complete search history.

(56) References Cited

U.S. PATENT DOCUMENTS

| | | | | |
|---|---|---|---|---|
| 5,922,604 | A * | 7/1999 | Stapleton et al. | 436/46 |
| 6,147,198 | A * | 11/2000 | Schwartz | 536/23.1 |
| 6,221,592 | B1 * | 4/2001 | Schwartz et al. | 435/6 |
| 6,326,211 | B1 * | 12/2001 | Anderson et al. | 436/177 |
| 6,355,491 | B1 * | 3/2002 | Zhou et al. | 436/518 |
| 6,448,012 | B1 * | 9/2002 | Schwartz | 435/6 |
| 6,827,831 | B1 * | 12/2004 | Chow et al. | 204/604 |
| 6,876,574 | B2 * | 4/2005 | Giebeler et al. | 365/158 |
| 7,312,029 | B1 * | 12/2007 | Hyde et al. | 435/4 |
| 2003/0102154 | A1 | 6/2003 | Haba | |
| 2004/0029152 | A1 * | 2/2004 | Ishida | 435/6 |
| 2004/0166025 | A1 | 8/2004 | Chan et al. | |
| 2004/0241699 | A1 * | 12/2004 | Zocchi et al. | 435/6 |
| 2005/0151126 | A1 * | 7/2005 | Yamakawa et al. | 257/22 |
| 2005/0158763 | A1 * | 7/2005 | Ivanisevic et al. | 435/6 |
| 2005/0221333 | A1 * | 10/2005 | Sundararajan et al. | 435/6 |
| 2006/0022952 | A1 | 2/2006 | Ryynanen | |
| 2007/0040191 | A1 * | 2/2007 | Bezryadin et al. | 257/213 |

OTHER PUBLICATIONS

Guan, Jingjiao; Lee, L. James; "Generating highly ordered DNA nanostrand arrays"; PNAS; Bearing a date of Dec. 20, 2005; pp. 18321-18325; vol. 102, No. 51; located at http://www.pnas.org/cgi/content/abstract/102/51/18321.

Heller, Daniel A.; Jeng, Esther S.; Yeung, Tsun-Kwan; Martinez, Brittany M.; "Optical Detection of DNA Conformational Polymorphism on Single-Walled Carbon Nanotubes"; Science; Bearing a date Jan. 27, 2006; pp. 508-511; vol. 311; located at www.sciencemag.org.

Physorg.com; "Biophysics: When chromosomes stretch"; Bearing dates of Apr. 26, 2006 and 2003-2006; printed on Jun. 16, 2006; pp. 1-3; located at http://physorg.com/news65273985,html.

Rogers, John A.; Nuzzo, Ralph G.; "Recent progess in soft lithography"; Materials Today; Bearing dates of Feb. 2005 and 2005; pp. 50-56; ISSN: 1369 7021; Elsevier Ltd.

Rothermund, Paul W.K.; "Folding DNA to create nanoscale shapes and patterns"; Nature; Bearing dates of Mar. 16, 2006 and 2006; pp. 297-302; vol. 440; Nature Publishing Group.

PCT International Search Report; International App. No. PCT/US07/15023; Dec. 5, 2008, pp. 1-2.

* cited by examiner

*Primary Examiner*—Ann Y Lam (57) ABSTRACT

Elongated molecules are stretched across a substrate by controlled fluid flow.

33 Claims, 6 Drawing Sheets

METHOD OF APPLYING AN ELONGATED MOLECULE TO A SURFACE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

1. For purposes of the USPTO extra-statutory requirements, the present application constitutes a continuation-in-part of U.S. patent application Ser. No. 11/480,763, entitled METHOD OF COMBING AN ELONGATED MOLECULE, naming Roderick A. Hyde and Lowell L. Wood, Jr. as inventors, filed 30 Jun. 2006, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/480,820, entitled METHOD OF COMBING A NUCLEIC ACID, naming Roderick A. Hyde and Lowell L. Wood, Jr. as inventors, filed 30 Jun. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a method of forming a nanowire includes applying a nucleic acid-containing solution to a first substrate that has a defined physical feature thereon, controllably flowing the nucleic acid-containing solution over the first substrate in a manner that promotes stretching of a nucleic acid molecule from the defined physical feature along the substrate, and applying a conductive material to the stretched nucleic acid molecule to form a nanowire. The nucleic acid may be DNA (e.g., mtDNA or cDNA), RNA (e.g., mRNA, tRNA, miRNA, or rRNA), or a synthetic nucleic acid (e.g., PNA, LNA, GNA, or TNA), may include chromosomes, viruses, plasmids, oligonucleotides, double-stranded nucleic acids, or single-stranded nucleic acids, and/or may be bound to a nanotube. The defined physical feature may be, for example, a depression or a protrusion. The substrate may include a plurality of defined physical features (e.g., in a repeating array), and nucleic acid molecules may extend from at least a subset of the plurality along the substrate. The method may further include transferring the stretched nucleic acid molecule to a second substrate, before or after applying the conductive material. Transferring may include bringing the first and second substrates into proximity or into contact, and may include controlling a surface charge of either or both substrates, where the surface charge may be attractive or repulsive, and may be spatially and/or temporally patterned. Alternatively or in addition, transferring may include controlling surface energy, temperature, and/or hydrophilicity of one or both of the substrates. The conductive material may be, for example, a metal, a semiconductor, a compound, or a polymer, and it may be substantially contiguous. The method may include applying a cover surface to the nucleic acid-containing solution, in which case controllably flowing may include moving the cover surface relative to the first substrate, for example by peeling or sliding the cover surface. The first substrate and/or the cover surface (if present) may include surface features that spatially direct the fluid flow, such as micro-orifices or switchable channels. The fluid that flows through the micro-orifices or switchable channels may be a liquid (such as the nucleic acid-containing solution) or a gas. Controllably flowing may include inducing surface charges (e.g., static, dynamic, and/or spatially patterned charges) on the first substrate and/or the cover surface (if present), for example by photoinducing surface charges. Alternatively or in addition, controllably flowing may include applying a varying surface tension (which may be temporally or spatially varied), applying an electromagnetic field (e.g., a pure electric field, a pure magnetic field, a plasmon, a static field, a dynamic field, and/or a spatially patterned field), controlling hydrophilicity (e.g., by varying hydrophilicity spatially and/or temporally), or varying temperature, and may include inducing vorticity into the nucleic acid-containing solution (which may promote deposition of a nucleic acid molecule in a curve along the first substrate). The nucleic acid-containing solution may include a mechanical anchor having a nucleic acid molecule anchored thereto, where the defined physical feature acts to spatially fix the mechanical anchor. The defined physical feature may include an anchored nucleic acid strand which hybridizes to a nucleic acid molecule in the nucleic acid-containing solution, in which case the method may further include dehybridizing the anchored strand and the hybridized nucleic acid.

In another aspect, a method of applying a nucleic acid to a surface includes applying a nucleic acid-containing solution to a first substrate having a defined physical feature including a nucleic acid anchor, and controllably flowing a deposition fluid (e.g., the nucleic acid-containing solution) over the first substrate in a manner that promotes stretching of a nucleic acid molecule from the defined physical feature along the first substrate. The nucleic acid may be DNA (e.g., mtDNA or cDNA), RNA (e.g., mRNA, tRNA, miRNA, or rRNA), or a synthetic nucleic acid (e.g., PNA, LNA, GNA, or TNA), may include chromosomes, viruses, plasmids, oligonucleotides, double-stranded nucleic acids, or single-stranded nucleic acids, and/or may be bound to a nanotube. The nucleic acid anchor may include an anchor strand of nucleic acid attached to the first substrate, which may hybridize with a nucleic acid molecule from the nucleic acid-containing solution. The nucleic acid-containing solution and/or the deposition solution may include a nucleic acid molecule bound to a mechanical anchor (e.g., a bead), and the nucleic acid anchor may include a trap (e.g., a depression or a protrusion) for the mechanical anchor. The trap may physically, electrically, and/or magnetically trap the mechanical anchor, and/or may adhere to it. The defined physical feature may be, for example, a depression or a protrusion. The substrate may include a plurality of defined physical features (e.g., in a repeating array), and nucleic acid molecules may extend from at least a subset of the plurality along the substrate. The method may further include transferring the stretched nucleic acid molecule to a second substrate, and may include applying a conductive material to the stretched nucleic acid molecule to form a nanowire, either before or after transferring the stretched nucleic acid molecule. Transferring may include bringing the first and second substrates into proximity or into contact, and may include controlling a surface charge of either or both substrates, where the surface charge may be attractive or repulsive, and may be spatially and/or temporally patterned. The second substrate may include an electronic device in electrical communication with the transferred nucleic acid molecule. The method may further include attaching an electronic device to the transferred nucleic acid molecule. The method may further include controlling a surface charge of the first substrate, where the controlled surface charge acts to attract and/or to repel the nucleic acid molecule from the first substrate. Controllably flowing may include applying a cover surface to the deposition fluid, and may further include moving the cover surface relative to the first substrate, for example by peeling or sliding the cover surface. The first substrate and/or the cover surface (if present) may include surface features that spatially direct the fluid flow, such as micro-orifices or switchable channels. The fluid that flows through the micro-orifices or switchable channels may be a liquid (such as the nucleic acid-containing solution and/or the deposition solution) or a gas. Controllably flowing may include inducing surface charges (e.g., static, dynamic, and/or spatially patterned charges) on the first substrate and/or the cover surface (if present), for example by photoinducing surface charges. Alternatively or in addition, controllably flowing may include applying a varying surface tension (which may be temporally or spatially varied), applying an electromagnetic field (e.g., a pure electric field, a pure magnetic field, a plasmon, a static field, a dynamic field, and/or a spatially patterned field), controlling hydrophilicity (e.g., by varying hydrophilicity spatially and/or temporally), or varying temperature, and may include inducing vorticity into the deposition fluid (which may promote deposition of a nucleic acid molecule in a curve along the substrate).

In a further aspect, a method of applying an elongated molecule to a surface includes controllably flowing a solution containing an elongated molecule over a first substrate in a manner that promotes stretching the elongated molecule from a defined physical feature along the first substrate. The elongated molecule is selected from the group consisting of polymers (e.g., isotactic polymers, atactic polymers, stereotactic polymers, thermoplastics, thermosets, elastomers, copolymers, block copolymers, organic polymers, inorganic polymers, polyamides, polyesters, polycarbonates, polyethers, polyimides, polyimines, formaldehydes, polysulfones, polyurethanes, polyvinyls, polyolefins, and/or polyalkynes), nanotubes, proteins (e.g., antibodies, enzymes, hormones, structural proteins, regulatory proteins, filamentous proteins, soluble proteins, motor proteins, denatured proteins, and/or polypeptides), carbohydrates (e.g., monosaccharides, disaccharides, oligosaccharides, polysaccharides, starches, glycogens, cellulose, amylose, and/or chitin), lipids (e.g., fatty acids, glycerides, phosphoglycerides, sphingolipids, steroids, waxes, lipoproteins, and/or glycolipids), and functionalized forms of any of the above. The defined physical feature may be, for example, a depression or a protrusion. The first substrate may include a plurality of defined physical features (e.g., in a repeating array), and elongated molecules may extend from at least a subset of the plurality along the substrate. The method may further include applying a conductive material (e.g., a metal, a semiconductor, a compound, and/or a polymer) to the stretched elongated molecule. The conductive material may be substantially contiguous. The method may further include transferring the stretched elongated molecule to a second substrate. A conductive material (e.g., a metal, a semiconductor, a compound, and/or a polymer) may be applied to the stretched elongated molecule before or after transfer, and the conductive material may be substantially contiguous. Transferring may include bringing the first and second substrates into proximity or into contact, and may include controlling a surface charge of either or both substrates, where the surface charge may be attractive or repulsive, and may be spatially and/or temporally patterned. Alternatively or in addition, transferring may include controlling surface energy, temperature, and/or hydrophilicity of one or both of the substrates. The second substrate may include an electronic device in electronic communication with the transferred elongated molecule. The method may further include attaching an electronic device to the transferred elongated molecule. The method may include applying a cover surface to the solution, in which case controllably flowing may include moving the cover surface relative to the first substrate, for example by peeling or sliding the cover surface. The first substrate and/or the cover surface (if present) may include surface features that spatially direct the fluid flow, such as micro-orifices or switchable channels. The fluid that flows through the micro-orifices or switchable channels may be a liquid (such as the solution containing the elongated molecule) or a gas. Controllably flowing may include inducing surface charges (e.g., static, dynamic, and/or spatially patterned charges) on the first substrate and/or the cover surface (if present), for example by photoinducing surface charges. Alternatively or in addition, controllably flowing may include applying a varying surface tension (which may be temporally or spatially varied), applying an electromagnetic field (e.g., a pure electric field, a pure magnetic field, a plasmon, a static field, a dynamic field, and/or a spatially patterned field), controlling hydrophilicity (e.g., by varying hydrophilicity spatially and/or temporally), or varying temperature, and may include inducing vorticity into the solution (which may promote deposition of an elongated molecule in a curve along the first substrate). The solution may include a mechanical anchor (e.g., a bead) having the elongated molecule anchored thereto, and the defined physical feature may act to spatially fix the mechanical anchor (e.g., by physically trapping, electrically trapping, magnetically trapping, and/or adhering to the mechanical anchor).

In yet another aspect, a method of applying an elongated molecule to a surface includes applying a solution containing the elongated molecule to a first substrate, and controllably flowing a deposition fluid over the first substrate in a manner that promotes stretching of the elongated molecule along the first substrate. Controllably flowing the deposition fluid includes flowing the deposition fluid in a configuration in which a surface of the deposition fluid is unconstrained. The elongated molecule may be a polymer (e.g., isotactic polymers, atactic polymers, stereotactic polymers, thermoplastics, thermosets, elastomers, copolymers, block copolymers, organic polymers, inorganic polymers, polyamides, polyesters, polycarbonates, polyethers, polyimides, polyimines, formaldehydes, polysulfones, polyurethanes, polyvinyls, polyolefins, and/or polyalkynes), a nanotube, a protein (e.g., antibodies, enzymes, hormones, structural proteins, regulatory proteins, filamentous proteins, soluble proteins, motor proteins, denatured proteins, and/or polypeptides), a carbohydrate (e.g., monosaccharides, disaccharides, oligosaccharides, polysaccharides, starches, glycogens, cellulose, amylose, and/or chitin), a lipid (e.g., fatty acids, glycerides, phosphoglycerides, sphingolipids, steroids, waxes, lipoproteins, and/or glycolipids), a nucleic acid (e.g., chromosomes, viruses, plasmids, oligonucleotides, naturally-occurring nucleic acids, synthetic nucleic acids, double-stranded nucleic acids, single-stranded nucleic acids, DNA, RNA, PNA, LNA, GNA, TNA, and/or nucleic acids bound to nanotubes), or a functionalized form of any of the above. The first substrate may include at least one defined physical feature, and controllably flowing may promote stretching of the elongated molecule from the defined physical feature along the first substrate. The first substrate may include a plurality of defined physical features (e.g., in a repeating array), where a plurality of elongated molecules may extend from at least a subset of the plurality of defined physical features along the first substrate. The method may further include transferring the stretched elongated molecule to a second substrate. A conductive material (e.g., a metal, a semiconductor, a compound, and/or a polymer) may be applied to the stretched elongated molecule before or after transfer, and the conductive material may be substantially contiguous. Transferring may include bringing the first and second substrates into proximity or into contact, and may include controlling a surface charge of either or both substrates, where the surface charge may be attractive or repulsive, and may be spatially and/or temporally patterned. The second substrate may include an electronic device in electronic communication with the transferred elongated molecule. The method may further include attaching an electronic device to the transferred elongated molecule. The deposition fluid may be the solution containing the elongated molecule. The first substrate may include surface features that spatially direct the fluid flow, such as micro-orifices or switchable channels. The fluid that flows through the micro-orifices or switchable channels may be a liquid (such as the solution containing the elongated molecule and/or the deposition fluid) or a gas. Controllably flowing may include inducing surface charges (e.g., static, dynamic, and/or spatially patterned charges) on the first substrate, for example by photoinducing surface charges. Alternatively or in addition, controllably flowing may include applying a varying surface tension (which may be temporally or spatially varied), applying an electromagnetic field (e.g., a pure electric field, a pure magnetic field, a plasmon, a static field, a dynamic field, and/or a spatially patterned field), controlling hydrophilicity (e.g., by varying hydrophilicity spatially and/or temporally), or varying temperature, and may include inducing vorticity into the solution (which may promote deposition of an elongated molecule in a curve along the first substrate).

In still another aspect, a method of applying an elongated molecule to a surface includes applying a solution containing the elongated molecule to a first substrate, and controllably flowing a deposition fluid over the first substrate in a manner that promotes stretching of the elongated molecule along the first substrate. Controllably flowing the deposition fluid includes flowing the deposition fluid in a configuration in which a surface of the deposition fluid maintains a substantially fixed distance from the first substrate. The elongated molecule may be a polymer (e.g., isotactic polymers, atactic polymers, stereotactic polymers, thermoplastics, thermosets, elastomers, copolymers, block copolymers, organic polymers, inorganic polymers, polyamides, polyesters, polycarbonates, polyethers, polyimides, polyimines, formaldehydes, polysulfones, polyurethanes, polyvinyls, polyolefins, and/or polyalkynes), a nanotube, a protein (e.g., antibodies, enzymes, hormones, structural proteins, regulatory proteins, filamentous proteins, soluble proteins, motor proteins, denatured proteins, and/or polypeptides), a carbohydrate (e.g., monosaccharides, disaccharides, oligosaccharides, polysaccharides, starches, glycogens, cellulose, amylose, and/or chitin), a lipid (e.g., fatty acids, glycerides, phosphoglycerides, sphingolipids, steroids, waxes, lipoproteins, and/or glycolipids), a nucleic acid (e.g., chromosomes, viruses, plasmids, oligonucleotides, naturally-occurring nucleic acids, synthetic nucleic acids, double-stranded nucleic acids, single-stranded nucleic acids, DNA, RNA, PNA, LNA, GNA, TNA, and/or nucleic acids bound to nanotubes), or a functionalized form of any of the above. The first substrate may include at least one defined physical feature, and controllably flowing may promote stretching of the elongated molecule from the defined physical feature along the first substrate. The first substrate may include at least one defined physical feature, and controllably flowing may promote stretching of the elongated molecule from the defined physical feature along the first substrate. The first substrate may include a plurality of defined physical features (e.g., in a repeating array), where a plurality of elongated molecules may extend from at least a subset of the plurality of defined physical features along the first substrate. The method may further include transferring the stretched elongated molecule to a second substrate. A conductive material (e.g., a metal, a semiconductor, a compound, and/or a polymer) may be applied to the stretched elongated molecule before or after transfer, and the conductive material may be substantially contiguous. Transferring may include bringing the first and second substrates into proximity or into contact, and may include controlling a surface charge of either or both substrates, where the surface charge may be attractive or repulsive, and may be spatially and/or temporally patterned. The second substrate may include an electronic device in electronic communication with the transferred elongated molecule. The method may further include attaching an electronic device to the transferred elongated molecule. The deposition fluid may be the solution containing the elongated molecule. The method may include applying a cover surface to the solution, in which case controllably flowing may include moving the cover surface relative to the first substrate, for example by sliding the cover surface. The first substrate and/or the cover surface (if present) may include surface features that spatially direct the fluid flow, such as micro-orifices or switchable channels. The fluid that flows through the micro-orifices or switchable channels may be a liquid (such as the solution containing the elongated molecule and/or the deposition fluid) or a gas. Controllably flowing may include inducing surface charges (e.g., static, dynamic, and/or spatially patterned charges) on the first substrate and/or the cover surface (if present), for example by photoinducing surface charges. Alternatively or in addition, controllably flowing may include applying a varying surface tension (which may be temporally or spatially varied), applying an electromagnetic field (e.g., a pure electric field, a pure magnetic field, a plasmon, a static field, a dynamic field, and/or a spatially patterned field), controlling hydrophilicity (e.g., by varying hydrophilicity spatially and/or temporally), or varying temperature, and may include inducing vorticity into the solution (which may promote deposition of an elongated molecule in a curve along the first substrate).

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
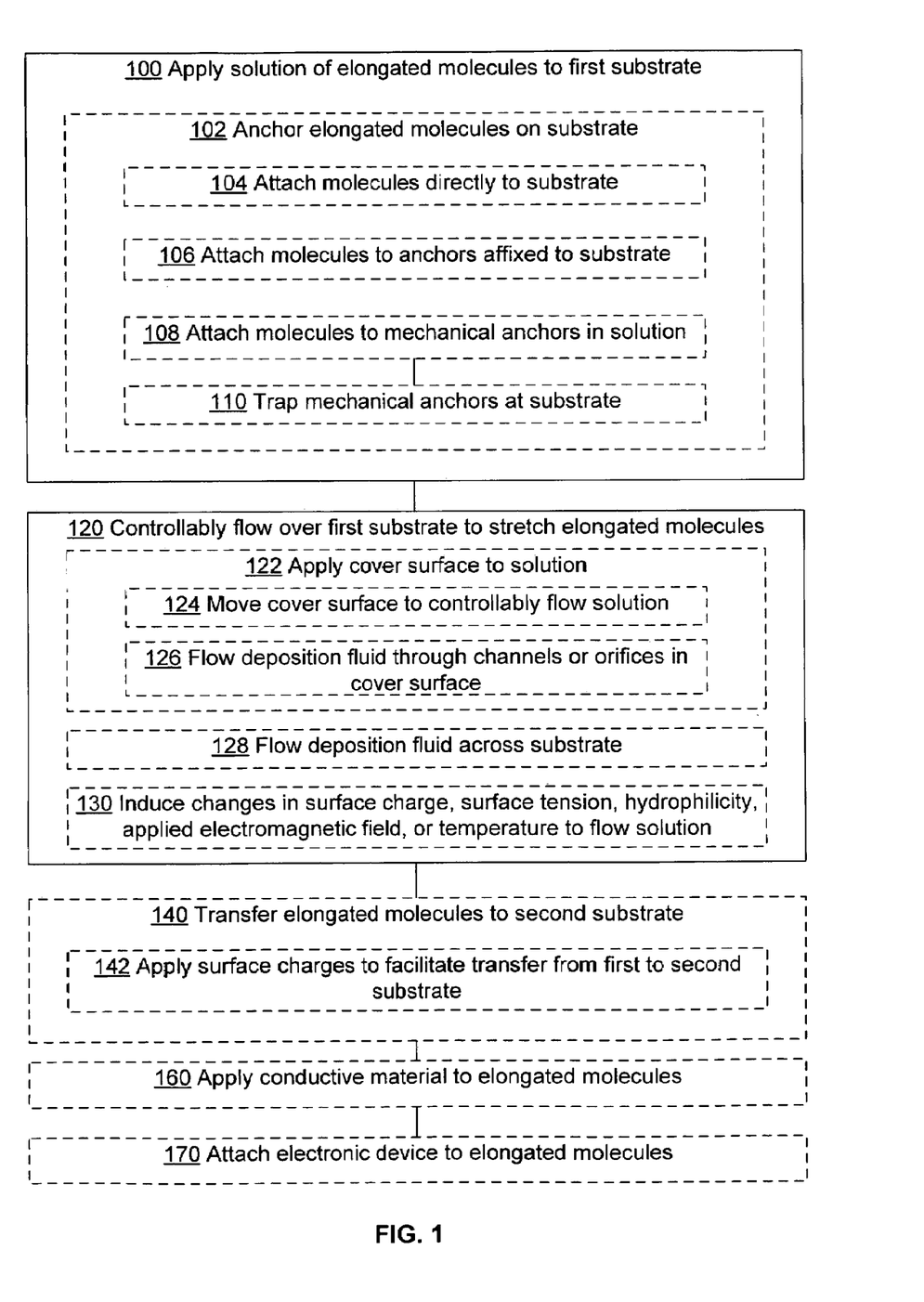
FIG. 1 is a flowchart illustrating methods of placing elongated molecules on a substrate.

FIG. 1 illustrates several embodiments of methods of placing nanometer-scale arrangements of elongated molecules on a substrate. Broadly, the methods include applying a solution of elongated molecules to a first substrate (block 100), and controllably flowing a deposition fluid (which may be the solution of elongated molecules) over the first substrate to stretch the elongated molecules (block 120). In some embodiments, the elongated molecules may be metallized or otherwise rendered conductive by application of a conductive material (block 160). In these or other embodiments, the elongated molecules may be transferred to a second substrate (block 140), for example using soft lithography techniques (see, e.g., Rogers, et al., "Recent progress in soft lithography," Mat. Today, 8(2):50-56 (February 2005), which is incorporated herein by reference). When the elongated molecules are metallized or otherwise coated with a conductive composition, this coating may occur before or after the transfer to the second substrate. In some embodiments, the elongated molecules may be attached to an electronic device (block 170).

One method for producing nanometer-scale arrays of DNA molecules is presented in Guan, et al., "Generating highly ordered DNA nanostrand arrays," Proc. Nat'l Acad. Sci., 102 (51):18321-18325 (December 2005), which is incorporated herein by reference. As shown therein, a DNA-containing solution is deposited on a glass slide, and a flexible poly (dimethyl siloxane) (PDMS) stamp is applied to the solution. When the flexible stamp is peeled away from the substrate, the DNA in the solution elongates along and adheres to the stamp, creating an arrangement of parallel strands. (This process is referred to as "combing" the DNA.) The stamp is patterned with an array of depressions, so that the DNA extends along the stamp from one depression to the next. The stamp is then applied to another surface, transferring the DNA thereto. The transferred DNA may be arranged in a regular array of fixed length strands corresponding to the spacing of the depressions on the stamp.

While the method presented in Guan focuses on application of DNA nanostrands to a substrate, for example for large-scale and highly automated analysis, the combed DNA strands may also be metallized (or coated with a nonmetallic conductor) to produce a regular array of nanoscale conductive segments. (In other embodiments, elongated molecules other than nucleic acids may be used, which may be intrinsically conductive.) This array may be used as a sort of "nanoscale breadboard" for construction of nanoscale circuits. In some embodiments, the regular array may mimic traditional breadboard layouts, while in others it may differ, for example to facilitate unique requirements of nanoscale circuits. The ability to position nucleic acid strands of known sequence, as further discussed below, may facilitate self-assembly of complex circuits by allowing circuit elements to be bound to known locations on a substrate.

In particular, in some embodiments, the arrangements of elongated molecules may be connected to the nanotube-based transistors and other circuit elements described in copending and commonly owned U.S. patent application Ser. Nos. 11/314,738, filed Dec. 20, 2005 and entitled "Deletable Nanotube Circuit," 11/314,718, filed Dec. 20, 2005 and entitled "Connectible Nanotube Circuit," and 11/314,751, filed Dec. 20, 2005 and entitled "Nanotube Circuit Analysis System and Method," all of which are incorporated herein by reference. In some embodiments, nanotube-based circuit elements may be "wrapped" with helical nucleic acids, as described in Heller, et al., "Optical Detection of DNA Conformational Polymorphism on Single-Walled Carbon Nanotubes," Science 311:508-511, January 2006, which is incorporated herein by reference. These elements may then be selectively placed at desired locations on a "breadboard" substrate as described above, by hybridization with nucleic acids fixed at selected locations on the surface to self-assemble a circuit. Rothemund, "Folding DNA to create nanoscale shapes and patterns," Nature 440:297-302, March 2006, incorporated herein by reference, describes another self-assembly technique in which structures are created having localized nucleic acid sequences. These structures may be used as nucleic acid anchors (further discussed below) for placement of nucleic acid molecules to be "combed," or as guides for placement of nanotube-based circuit elements.

A variety of elongated molecules may be applied to substrates as discussed below, such as nucleic acid molecules, including without limitation DNA such as mtDNA or cDNA, RNA such as mRNA, tRNA, miRNA, or rRNA, synthetic nucleic acids such as PNA, LNA, GNA, or TNA, chromosomes, viruses, plasmids, and oligonucleotides, any of which may be in single-stranded or double-stranded form, and any of which may be bound to other structures such as nanotubes (for example, a DNA-wrapped nanotube is described in Heller, supra), may be applied to substrates as discussed below. Other elongated molecules that may be applied to a substrate in the same manner include polymers (e.g., isotactic polymers, atactic polymers, stereotactic polymers, thermoplastics, thermosets, elastomers, copolymers, block copolymers, organic polymers, inorganic polymers, polyamides, polyesters, polycarbonates, polyethers, polyimides, polyimines, formaldehydes, polysulfones, polyurethanes, polyvinyls, polyolefins, and/or polyalkynes), nanotubes, proteins (e.g., antibodies, enzymes, hormones, structural proteins, regulatory proteins, filamentous proteins, soluble proteins, motor proteins, denatured proteins, and/or polypeptides), carbohydrates (e.g., monosaccharides, disaccharides, oligosaccharides, polysaccharides, starches, glycogens, cellulose, amylose, and/or chitin), lipids (e.g., fatty acids, glycerides, phosphoglycerides, sphingolipids, steroids, waxes, lipoproteins, and/or glycolipids), or modified or functionalized forms of any of these.

Application of the solution of elongated molecules to the first substrate may include anchoring the elongated molecules to the substrate (block 102), for example by anchoring them to defined physical features of the substrate. In some embodiments, the elongated molecules may adhere directly to the substrate (block 104). In other embodiments, the elongated molecules may adhere to anchors which are affixed to the substrate (block 106). In still other embodiments, the elongated molecules may be attached (block 108) to mechanical anchors (e.g., beads) in the solution (or in a separate deposition fluid), and those anchors may be trapped at the substrate (block 110) by a variety of means (e.g., physically, chemically, electrically, and/or magnetically).

Controlled flow over the first substrate stretches the elongated molecules along the substrate (block 120), usually but not necessarily along the path of controlled flow over the substrate. A variety of methods are contemplated for controlling flow. In some embodiments, a cover surface is applied to the solution containing the elongated molecules (block 122). This surface may then be moved (block 124) to controllably flow the solution (e.g., by peeling it away from the substrate or sliding it along the substrate). Alternatively or in addition, the cover surface may comprise channels or micro-orifices, and a deposition fluid (which may be the solution of elongated molecules) may be flowed through the channels or orifices (block 126). In other embodiments, a deposition fluid may flow across the substrate (block 128). Flow (in the solution or in another deposition fluid) may also be controlled by inducing patterns in surface charge, surface tension, hydrophilicity, applied electromagnetic field, and/or temperature.

Optionally, the stretched elongated molecules may be transferred to a second substrate (block 140). In some embodiments, this transfer may be facilitated or controlled by application of surface charges to the first and/or the second substrate (block 142). Conductive material may be applied to the elongated molecules either before or after transfer (block 160), and an electronic device (e.g., a transistor such as a carbon nanotube transistor) may be attached to the stretched elongated molecule (block 170) before or after any transfer and before or after any application of conductive material.

FIGS. 2-16 illustrate several exemplary embodiments of the above-described methods. These examples should be considered illustrative only, as many other configurations of the described methods will be apparent to those skilled in the art.

Figure 2:
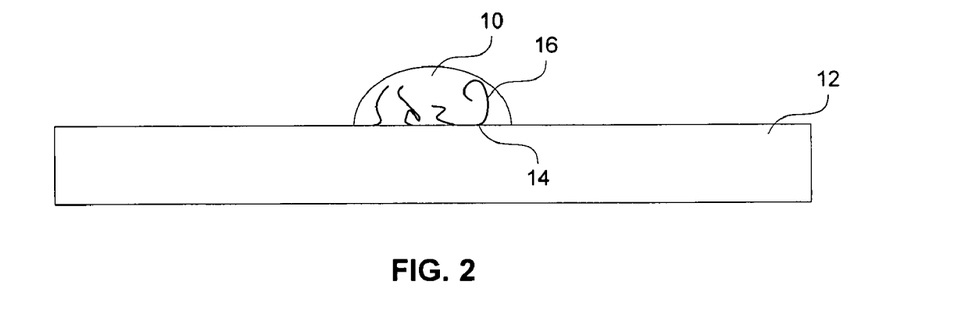
FIG. 2 shows a solution of elongated molecules applied to a substrate.
Figure 3:
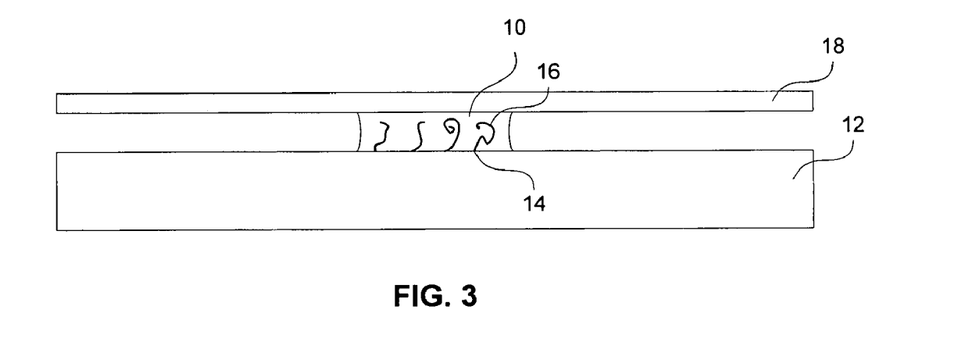
FIG. 3 shows a cover surface applied to the solution of FIG. 2.
Figure 4:
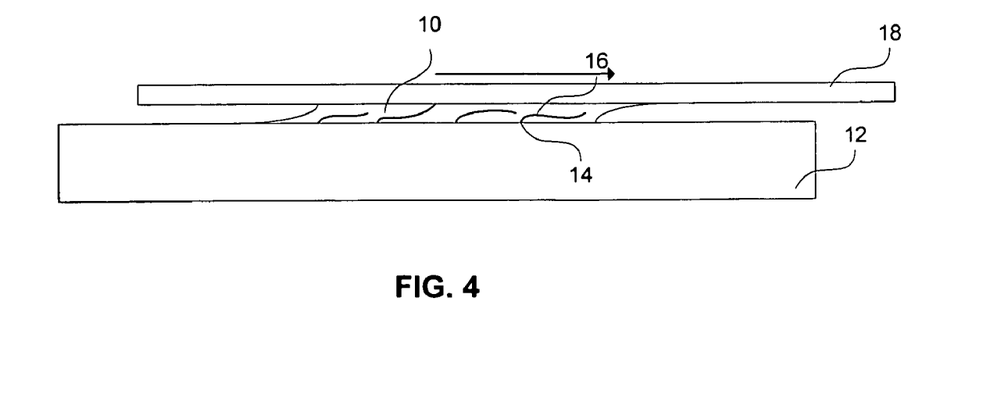
FIG. 4 shows stretching of the elongated molecules along the substrate.

As shown in FIG. 2, a solution 10 containing elongated molecules 16 is applied to a first substrate 12 having defined physical features 14. The solution is controllably flowed over the first substrate in a manner that promotes stretching of an elongated molecule 16 from the defined physical feature along the first substrate. In the embodiment shown in FIG. 3 and FIG. 4, this flow is accomplished by applying cover slip 18 to the solution 10 and sliding it along the first substrate 12 while maintaining a constant distance between the cover slip and the substrate, inducing flow parallel to the substrate 12. (Equivalently, the substrate may be moved while the cover surface is held still; "moving the cover surface relative to the substrate" is considered to include all configurations in which cover surface and/or substrate are moved relative to one another.) In other embodiments, this flow may be induced or controlled by other methods, and may involve a separate deposition fluid as discussed below. A conductive material (e.g., a metal, a semiconductor, a polymer, or a compound) may then be applied to the stretched elongated molecule 16 to form a nanowire. (The stretched molecules 16 may be transferred to a second substrate, as discussed below in connection with FIG. 7, either before or after the application of conductive material.) In some embodiments, the conductive coating may form a contiguous coating around the elongated molecule, while in other embodiments, the coating may be partial.

Figure 5:
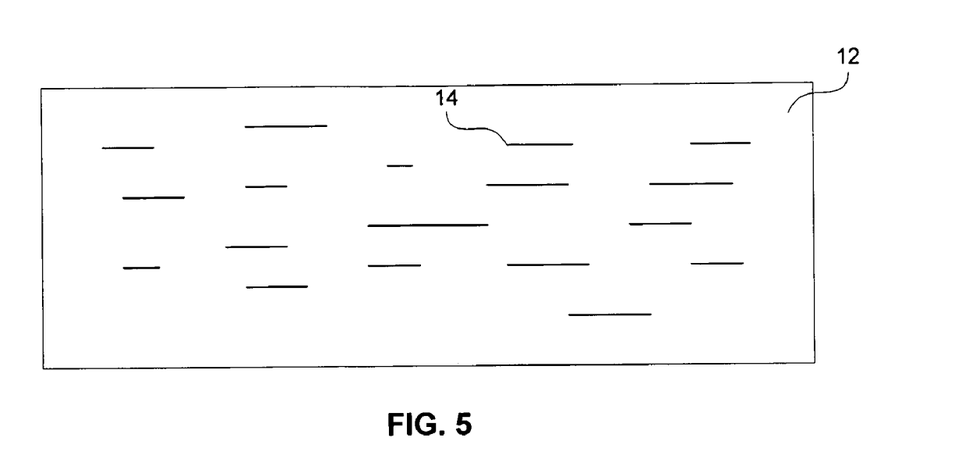
FIG. 5 shows an irregular arrangement of stretched elongated molecules.
Figure 6:
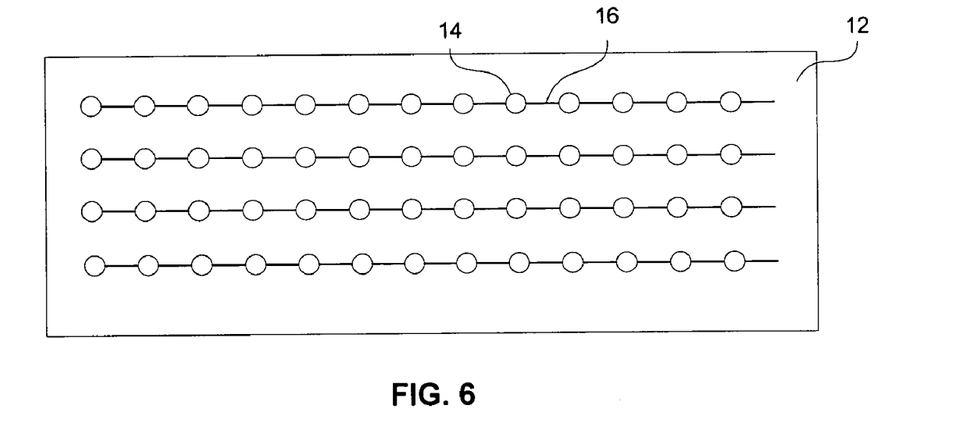
FIG. 6 shows a regular arrangement of stretched elongated molecules.

Defined physical features 14 may be distributed randomly on the first substrate 12 as shown in FIG. 5, in an ordered array as shown in FIG. 6, or in any other suitable arrangement for a particular embodiment. In the ordered array shown in FIG. 6, the defined features 14 are an arrangement of depressions. Elongated molecules 16 extend from each depression to an adjacent one. As discussed in Guan et al. (supra), if nucleic acid molecules are transferred to another substrate (e.g. by soft lithography), portions extending from one depression to the next may be selectively transferred to produce a regular array of nucleic acid molecules having a substantially uniform length. Other types of molecules may be similarly transferred, and other defined physical features such as protrusions and chemical or mechanical anchors may also be used.

Figure 7:
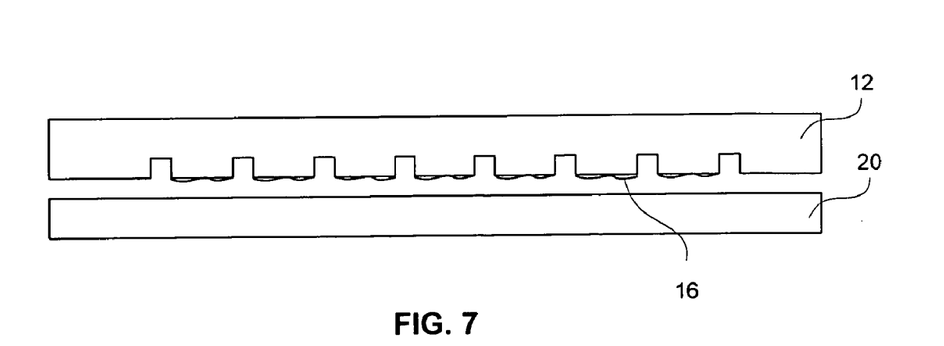
FIG. 7 shows stretched elongated molecules on a first substrate being transferred to a second substrate.

FIG. 7 illustrates the process of transferring elongated molecules 16 from the first substrate 12 to a second substrate 20, by placing the substrates in proximity to one another. (In Guan et al. (supra), the PDMS stamp was allowed to dry, and then was placed in contact with a flat surface for one minute.) In some embodiments, transfer from the first substrate 12 to the second substrate 20 may be enhanced by manipulating properties of either or both substrates such as the surface energy, the surface charge, the temperature, and/or the hydrophilicity of the substrates, or by the application of an electromagnetic field (e.g., a pure electric field, a pure magnetic field, a static field, a dynamic field, a spatially patterned field, and/or a plasmon). For example, a photoinduced surface charge may be used to repel the elongated molecules 16 from the first substrate 12, and/or to attract the elongated molecules to the second substrate 20, to enhance transfer. These surface charges may be uniform across the substrate(s), or they may be spatially patterned to enhance or inhibit transfer in localized areas. Depending on the properties of the substrates, transfer may occur even without direct contact between the first and second substrates.

Figure 8:
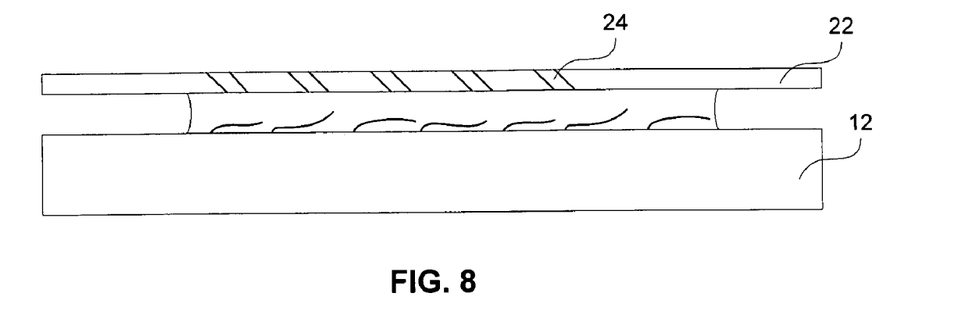
FIG. 8 shows a cover surface including a plurality of microorifices.

FIG. 8 illustrates an alternate embodiment for controllably flowing the solution over the first substrate. As shown, a cover surface 22 including a plurality of micro-orifices 24 is applied to the solution on the first substrate. A deposition fluid flowing through the micro-orifices 24 controls the flow of the solution. The deposition fluid may be the solution containing the elongated molecules, or it may be a separate fluid (which may be a liquid or a gas). In some embodiments, flow in the micro-orifices may be controlled by manipulating their surface charge, surface energy, temperature, and/or hydrophilicity, or by application of electromagnetic fields (e.g., a pure electric field, a pure magnetic field, a static field, a dynamic field, a spatially patterned field, and/or a plasmon).

Figure 9:
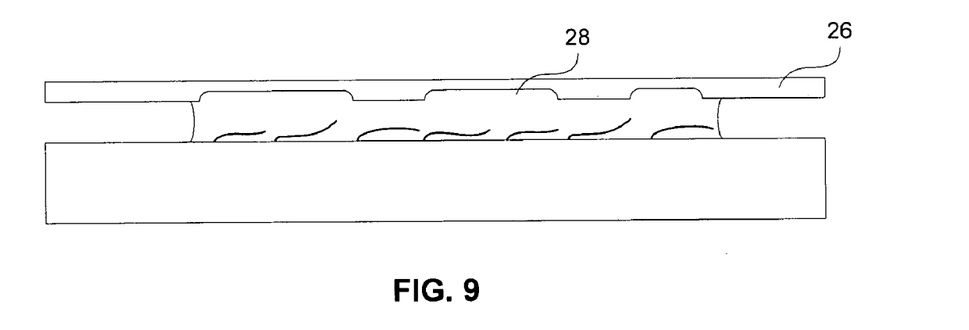
FIG. 9 shows a cover surface including a plurality of switchable channels.
Figure 10:
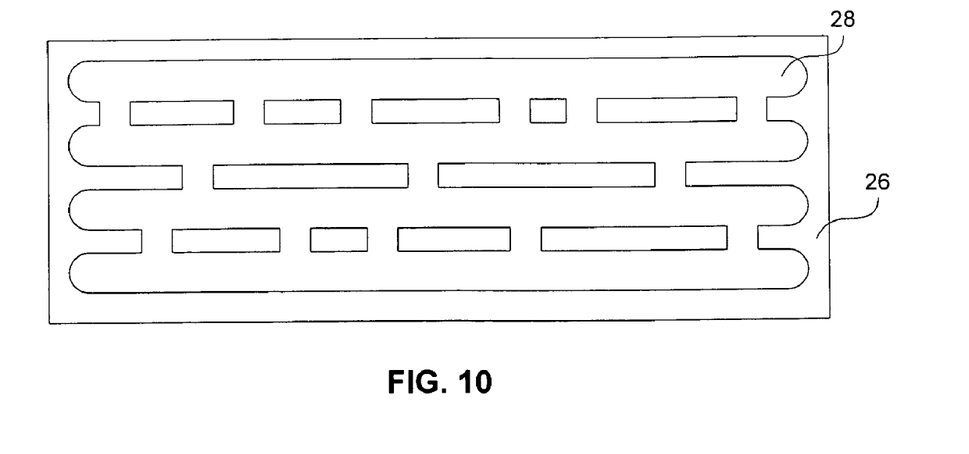
FIG. 10 shows a switchable channel layout.

FIG. 9 and FIG. 10 illustrate an additional embodiment for controllably flowing the solution over the first substrate. As shown in FIG. 9, a cover surface 26 including a plurality of channels 28 is applied to the solution on the first substrate. A detail of a channel 28 layout is shown in FIG. 10; however, many layouts are possible depending on the desired final arrangement of elongated molecules. A deposition fluid flowing through the channels controls the flow of the solution. The deposition fluid may be the solution containing the elongated molecules, or it may be a separate fluid (which may be a liquid or a gas). In some embodiments, flow in the channels may be controlled by manipulating their surface charge, surface energy, temperature, and/or hydrophilicity, or by application of electromagnetic fields (e.g., a pure electric field, a pure magnetic field, a static field, a dynamic field, a spatially patterned field, and/or a plasmon).

In some embodiments, flow along the first substrate may be controlled by manipulating the surface charge, surface energy, temperature, and/or hydrophilicity of the first substrate, even if the solution has a free surface, for example by photoinducing surface charges. Alternatively or in addition, flow may be controlled by similarly manipulating the properties of a cover slip such as that shown in FIG. 3 and FIG. 4. Electromagnetic fields (e.g., a pure electric field, a pure magnetic field, a static field, a dynamic field, a spatially patterned field, and/or a plasmon) may also be used to control flow, with or without a cover slip.

In some embodiments, controlling flow includes maintaining a laminar flow, while in other embodiments, controlling flow includes inducing vorticity into the solution. In either of these embodiments, elongated molecules may be deposited in a curve along the substrate. In some embodiments, the deposition fluid that is controllably flowed across the substrate may be the solution containing the elongated molecules, while in others, a separate deposition fluid may be used to "comb" the molecules after the solution has been placed on the substrate.

Figure 11:
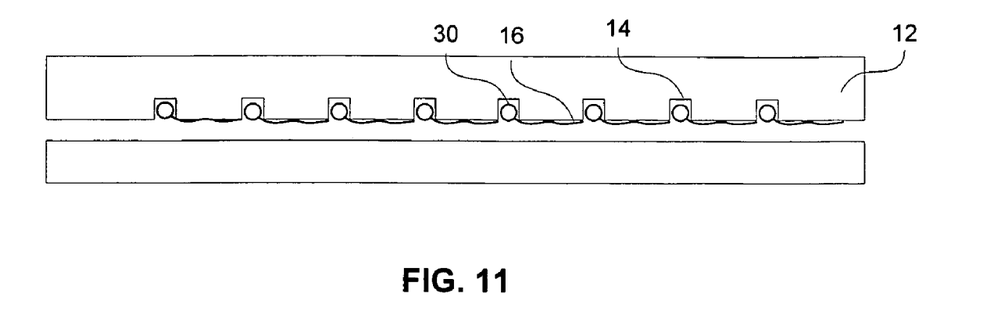
FIG. 11 shows a plurality of stretched elongated molecules bound to a plurality of mechanical anchors.

In another embodiment, illustrated in FIG. 11, elongated molecules 16 in solution may be bound to physical anchors 30 (such as beads). These beads may be trapped by the defined physical features 14 on the first substrate, shown in FIG. 11 as depressions that mechanically trap the beads. In other embodiments, the defined physical features may electrically or magnetically trap the physical anchors, or may adhere to the physical anchors (e.g., by hydrogen bonds, polar bonds, ionic bonds, dipole attraction, and/or covalent bonds). In some embodiments, this configuration may provide nucleic acid molecules or proteins having a known sequence at the surface of the substrate (since the molecules may be anchored to the bead at a known point in their sequence).

Figure 12:
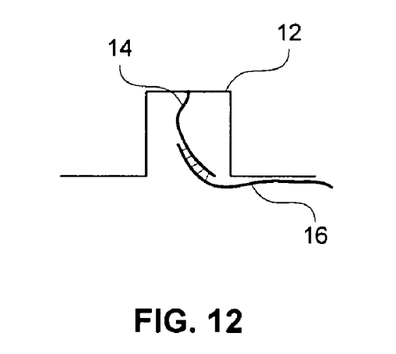
FIG. 12 shows a single-stranded nucleic acid used as an anchor.
Figure 13:
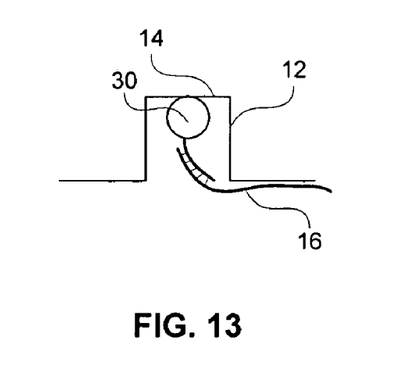
FIG. 13 shows a bead bound to a single-stranded nucleic acid used as an anchor.

As shown in FIG. 12, the defined physical features 14 at the surface of the first substrate may be single stranded nucleic acids bound to the first substrate 12. In another embodiment, shown in FIG. 13, single stranded nucleic acids may be bound to physical anchors such as beads 30, which are trapped by the defined physical features 14 of the first substrate as described in connection with FIG. 11. In either of these embodiments, when a nucleic acid-containing solution is controllably flowed across the first substrate, the localized strands (bound to the substrate or to the physical anchor) may then hybridize with complementary nucleic acids in the solution, anchoring the nucleic acids in place at one end (from which they may extend across the first substrate in the direction of the flow of the solution). This configuration may also provide nucleic acid molecules having a known sequence on the surface of the substrate, since the localized strands may have known sequences which will bind to specific sequences within the nucleic acid-containing solution. In some embodiments, the hybridized stretched nucleic acid molecule may then be dehybridized. For example, the hybridized stretched nucleic acid molecule may be dehybridized when a second substrate is brought into contact with (or into the vicinity of) the first substrate to facilitate transfer to the second substrate. In some such embodiments, the first substrate and its localized single strand anchors may be reusable.

Figure 14:
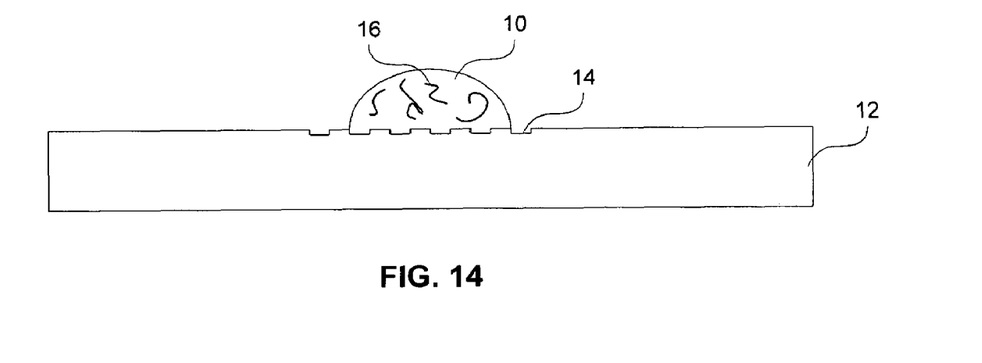
FIG. 14 shows a solution of free elongated molecules applied to a substrate.
Figure 15:
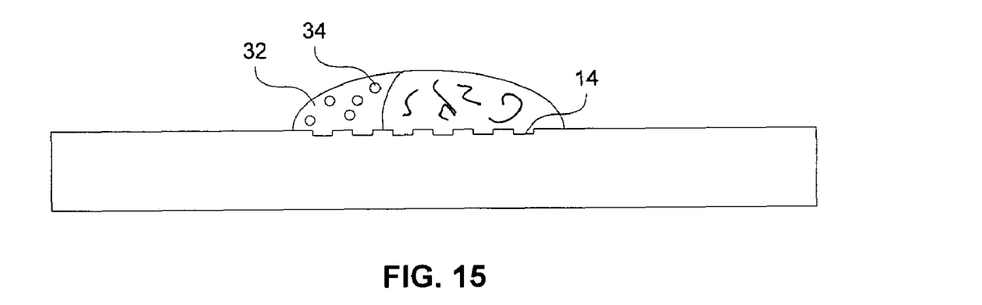
FIG. 15 shows a deposition fluid containing a plurality of mechanical anchors applied to the solution of FIG. 14.
Figure 16:
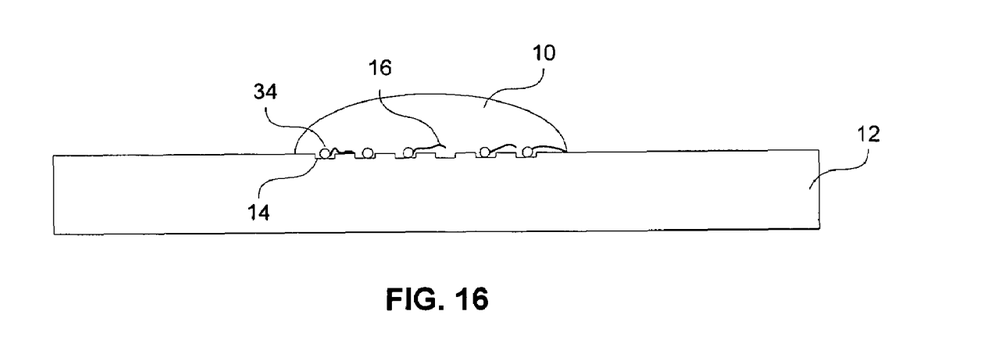
FIG. 16 shows the mechanical anchors of FIG. 15 bound to the elongated molecules and trapped at the substrate.

In another embodiment, shown in FIG. 14, a solution 10 containing elongated molecules 16 is applied to a first substrate 12 having defined physical features 14. A deposition fluid 32 containing mechanical anchors 34 is controllably flowed over the first substrate, as shown in FIG. 15 and FIG. 16. As the deposition fluid is flowed across the substrate, the mechanical anchors 34 bind to the elongated molecules 16 and are trapped by the defined physical features 14, which thus act as nucleic acid anchors. The elongated molecules extend from the trapped mechanical anchors 34 along the substrate as the deposition fluid flows.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of applying an elongated molecule to a surface, comprising:
    applying a solution containing the elongated molecule to a first substrate;
    applying a cover surface to the solution; and
    controllably flowing a deposition fluid over the first substrate in a manner that promotes stretching of the elongated molecule along the first substrate,
    wherein controllably flowing comprises sliding the cover surface relative to the first substrate to induce fluid flow in the deposition fluid.

2. The method of claim 1, wherein the elongated molecule is selected from the group consisting of polymers, nanotubes, proteins, carbohydrates, lipids, nucleic acids, and functionalized forms of any of the above.

3. The method of claim 1, wherein the first substrate has at least one defined physical feature, and wherein controllably flowing promotes stretching of the elongated molecule from the defined physical feature along the first substrate.

4. The method of claim 3, wherein the first substrate has a plurality of defined physical features, and wherein controllably flowing promotes stretching of a plurality of elongated molecules from at least a subset of the plurality of defined physical features along the first substrate.

5. The method of claim 4, wherein the defined physical features are arranged in a repeating array.

6. The method of claim 1, further comprising applying a conductive material to the stretched elongated molecule to form a nanowire.

7. The method of claim 1, wherein the deposition fluid is the solution containing the elongated molecule.

8. The method of claim 1, wherein the first substrate comprises surface features that spatially direct fluid flow.

9. The method of claim 1, wherein the surface features that spatially direct fluid flow comprise a plurality of micro-orifices, and wherein controllably flowing comprises flowing a fluid through at least a subset of the micro-orifices.

10. The method of claim 9, wherein the fluid that flows through the at least a subset of the micro-orifices is the solution containing the elongated molecule.

11. The method of claim 9, wherein the fluid that flows through the at least a subset of the micro-orifices is the deposition fluid.

12. The method of claim 9, wherein the fluid that flows through the at least a subset of the micro-orifices is a gas.

13. The method of claim 1, wherein the surface features that spatially direct fluid flow comprise a plurality of switchable channels, and wherein controllably flowing comprises switching at least a subset of the switchable channels.

14. The method of claim 1, wherein controllably flowing comprises inducing vorticity in the deposition fluid.

15. The method of claim 14, wherein the fluid flow promotes deposition of the elongated molecule in a curve along the first substrate.

16. The method of claim 1, wherein controllably flowing comprises directing fluid flow by applying a varying surface tension along the first substrate.

17. The method of claim 1, wherein controllably flowing comprises directing fluid flow by applying an electromagnetic field to the deposition fluid.

18. The method of claim 17, wherein the electromagnetic field is a pure electric field.

19. The method of claim 17, wherein the electromagnetic field is a pure magnetic field.

20. The method of claim 17, wherein the electromagnetic field is a plasmon.

21. The method of claim 17, wherein the electromagnetic field is a static field.

22. The method of claim 17, wherein the electromagnetic field is a dynamic field.

23. The method of claim 17, wherein the electromagnetic field is spatially patterned.

24. The method of claim 1, wherein controllably flowing comprises directing fluid flow by controlling hydrophilicity of the first substrate.

25. The method of claim 24, wherein controlling hydrophilicity of the first substrate comprises dynamically changing the hydrophilicity of the first substrate.

26. The method of claim 1, wherein at least one of the cover surface and the first substrate comprises features that spatially direct the fluid flow.

27. The method of claim 26, wherein the features that spatially direct fluid flow include a plurality of micro-orifices, and wherein controllably flowing comprises flowing a fluid through at least a subset of the micro-orifices.

28. The method of claim 27, wherein the fluid that flows through at least a subset of the micro-orifices is the deposition fluid.

29. The method of claim 27, wherein the fluid that flows through at least a subset of the micro-orifices is the solution containing the elongated molecule.

30. The method of claim 27, wherein the fluid that flows through at least a subset of the micro-orifices is a gas.

31. The method of claim 26, wherein the features that spatially direct fluid flow include a plurality of switchable channels, and wherein controllably flowing comprises switching at least a subset of the switchable channels.

32. The method of claim 1, wherein controllably flowing comprises inducing surface charges on at least one of the cover surface and the first substrate.

33. The method of claim 32, wherein inducing surface charges comprises photoinducing surface charges.

* * * * *

UNITED STATES PATENT AND TRADEMARK OFFICE
CERTIFICATE OF CORRECTION

PATENT NO. : 7,595,150 B2
APPLICATION NO. : 11/480779
DATED : September 29, 2009
INVENTOR(S) : Roderick A. Hyde and Lowell L. Wood, Jr.

It is certified that error appears in the above-identified patent and that said Letters Patent is hereby corrected as shown below:

Replace the word solution in line 48, column 12 in claim 12 with the following:

--deposition fluid--

Signed and Sealed this

Ninth Day of February, 2010

David J. Kappos
*Director of the United States Patent and Trademark Office*